United States Patent
Thorne et al.

(10) Patent No.: US 8,214,229 B2
(45) Date of Patent: Jul. 3, 2012

(54) METHOD AND SYSTEM FOR CREATING A NETWORK OF MEDICAL IMAGE READING PROFESSIONALS

(75) Inventors: Curtis J. Thorne, Nashville, TN (US); Gregg Phillip Allen, Franklin, TN (US)

(73) Assignee: Premerus, LLC, Franklin, TN (US)

( * ) Notice: Subject to any disclaimer, the term of this patent is extended or adjusted under 35 U.S.C. 154(b) by 433 days.

(21) Appl. No.: 12/365,787

(22) Filed: Feb. 4, 2009

(65) Prior Publication Data

US 2009/0204426 A1 Aug. 13, 2009

Related U.S. Application Data

(60) Provisional application No. 61/065,062, filed on Feb. 8, 2008, provisional application No. 61/065,055, filed on Feb. 8, 2008, provisional application No. 61/065,085, filed on Feb. 8, 2008, provisional application No. 61/065,061, filed on Feb. 8, 2008.

(51) Int. Cl.
*G06Q 10/00* (2006.01)
(52) U.S. Cl. .............................................. 705/2; 705/3
(58) Field of Classification Search ................... 705/2–3
See application file for complete search history.

(56) References Cited

U.S. PATENT DOCUMENTS

| | | | |
|---|---|---|---|
| 7,765,109 B2 | 7/2010 | Gutman et al. | |
| 7,831,445 B2 | 11/2010 | Reiner | |
| 2002/0010395 A1* | 1/2002 | Strawder | 600/407 |
| 2005/0187787 A1 | 8/2005 | Tomlinson, Jr. et al. | |
| 2005/0256743 A1 | 11/2005 | Dale | |
| 2006/0005347 A1 | 1/2006 | Griffin et al. | |
| 2006/0106640 A1 | 5/2006 | Deline | |
| 2006/0122865 A1 | 6/2006 | Preiss et al. | |
| 2006/0173663 A1 | 8/2006 | Langheier et al. | |
| 2006/0195339 A1 | 8/2006 | Backhaus et al. | |
| 2007/0011024 A1 | 1/2007 | Dale et al. | |
| 2007/0136355 A1 | 6/2007 | Haider | |
| 2007/0232868 A1* | 10/2007 | Reiner | 600/300 |
| 2007/0250352 A1 | 10/2007 | Tawil | |
| 2008/0004904 A1 | 1/2008 | Tran | |
| 2008/0306760 A1 | 12/2008 | Minnigh et al. | |
| 2009/0094058 A1 | 4/2009 | Reiner | |
| 2009/0132285 A1 | 5/2009 | Jakobovits | |

FOREIGN PATENT DOCUMENTS

| | | |
|---|---|---|
| WO | WO2006057953 | 1/2006 |
| WO | WO2007062523 | 7/2007 |
| WO | WO2007089686 A2 | 8/2007 |

OTHER PUBLICATIONS

Woodard et al, "Performance assessment for radiologists interpreting screening mammograph," Jul. 17, 2006, Wiley. InterScience, 26:1532-1551.

Notice of Allowance mailed Mar. 28, 2011 for U.S. Appl. No. 12/365,796.

(Continued)

*Primary Examiner* — Lena Najarian
(74) *Attorney, Agent, or Firm* — SNR Denton US, LLP

(57) ABSTRACT

A method and system is provided for creating a network of medical image reading professionals who are highly skilled and proficient at reading and interpreting medical images. By creating such a network of medical image reading professionals, misdiagnoses can be dramatically reduced, thereby improving patient outcomes, reducing patient suffering and anxiety, reducing costs, and reducing the overall burden on the healthcare system.

17 Claims, 4 Drawing Sheets

OTHER PUBLICATIONS

Amendment after Allowance filed Jun. 23, 2011 for U.S. Appl. No. 12/365,796.
Response to amendment after Notice of Allowance mailed Jul. 28, 2011 for U.S. Appl. No. 12/365,796.
Request of Continuted Prosecution Aug. 3, 2011 for U.S. Appl. No. 12/365,796.
Supplemental Notice of Allowance Aug. 24, 2011 for U.S. Appl. No. 12/365,796.
Non-Final Rejection mailed Aug. 26, 2011 for U.S. Appl. No. 12/365,815.
Amendment after Non-Final Rejection filed Nov. 28, 2011 for U.S. Appl. No. 12/365,815.
Notice of Allowance mailed Dec. 28, 2011 for U.S. Appl. No. 12/365,815.
Non-Final Rejections mailed Aug. 12, 2011 for U.S. Appl. No. 12/365,824.
Amendment after Non-Final Rejection filed Nov. 14, 2011 for U.S. Appl. No. 12/365,824.
Final Rejection mailed Dec. 30, 2011 for U.S. Appl. No. 12/365,824.
Restriction Requirement mailed Dec. 28, 2011 U.S. Appl. No. 13/167,579.
Response to Restriction Requirement Jan. 26, 2010 U.S. Appl. No. 13/167,579.

* cited by examiner

METHOD AND SYSTEM FOR CREATING A NETWORK OF MEDICAL IMAGE READING PROFESSIONALS

CROSS-REFERENCE TO RELATED APPLICATIONS

This application claims priority to the following U.S. Provisional Patent Applications: Ser. No. 61/065,062 filed on Feb. 8, 2008; 61/065,055 filed on Feb. 8, 2008; 61/065,085 filed on Feb. 8, 2008; and 61/065,061 filed on Feb. 8, 2008; the entire teachings of which are herein incorporated by reference.

BACKGROUND

The practice of medicine has greatly advanced with the improvement of medical imaging technology. Medical imaging may include many different types of image of the human body, including x-ray imaging, computed tomography (CT) scan imaging, magnetic resonance imaging (MRI), etc. Through the use of medical imaging technology, medical professionals are able to see images of internal organs, for example, of patients to help diagnose medical conditions of the patients. While medical imaging technology has significantly improved medical care, because of the nature of creating and interpreting medical images, radiological or other imaging technique, inaccuracies in the imaging and interpretation processes of the medical images result. Because of the inaccuracies in the imaging and interpretation processes, patient medical conditions are often misdiagnosed.

Misdiagnosis of a medical condition, such as a disease, may come in the form of false positives, false negatives, and false equivocal diagnoses. A false positive is, a detection of a disease that does not exist. A false negative is a failure to detect a disease that is present in a patient. A false equivocal diagnosis is a statement that a definitive diagnosis cannot be made based on the information available (e.g., "cancer cannot be ruled out") when sufficient information is available to make a definitive diagnosis. Each of these misdiagnoses may result in higher costs of treatment, additional suffering to patients, lost productivity, exposure to treatments which themselves have side effects that diminish health status, and additional burden on the healthcare system as a whole. It has been estimated by the American College of Radiology that frequency of misdiagnosis of radiological imaging interpretations is as high as 30%. And, given that it has been estimated that 40% to 60% of total healthcare spend is influenced by radiological imaging and interpretations therefrom, misdiagnoses results from misinterpretation of medical imaging has a large impact on the healthcare system.

Medical literature documents significant variation in misdiagnosis rates among medical image reading professionals. Much of the misdiagnoses in reading medical images occurs from medical image reading professionals either not having enough experience or not having enough experience reading particular types of medical conditions. For example, a large scale study of proficiency in reading screening mammography studies concluded that false negative findings range from 3% to 71% (mean of 23%) and false positive findings range from 1% to 29% (mean of 10%), and that the higher overall accuracy was associated with more experience and a higher focus on screening mammograms. It is therefore reasonably predictable that a general radiologist who reads relatively few mammograms while attending to the broad range of clinical radiology needs of a rural community in which he or she resides, reading medical images for brain tumors, small cell lung cancer, or other diseases. Because of the broad nature of the clinical practice, the general radiologist is more likely to misdiagnose both mammograms and other medical conditions where experience is not sufficient to attain proficiency.

SUMMARY

To overcome the problems that result from misdiagnosis of medical conditions of patients, the principles of the present invention provide for creating a network of medical image reading professionals who are highly skilled and proficient at reading and interpreting medical images. By creating such a network of medical image reading professionals, the problem of misdiagnosis can be dramatically reduced, thereby improving patient outcomes, reducing patient suffering and anxiety, reducing costs, and reducing the overall burden on the healthcare system.

One embodiment of a system and method for creating a network of medical image reading professionals may include selecting a medical image reading professional candidate who meets at least one acceptance criteria, where the criteria may have predictive value in assessing the proficiency of the reading professional in providing accurate diagnoses. For various imaging modalities, a list of expertise areas may be provided for the selected medical image reading professional candidate to select at least one expertise area to identify him or herself as a participant in a network of medical image reading professionals. Sets of medical images of the selected anatomical region(s) may be distributed to the medical image reading professional candidate. Diagnostic proficiency of the medical image reading professional candidate in interpreting information presented in the distributed sets of medical images may be tested. A determination may be made as to whether the medical image reading professional candidate qualifies to participate in the network of medical image reading professionals for the selected anatomical region(s) based on the diagnostic proficiency of the medical image reading professional candidate in reading and diagnosing information presented in the distributed sets of medical images. If the medical image reading professional candidate qualifies to participate in the network of medical image reading professionals, the medical image reading professional candidate may be included in the network of medical image reading professionals to enable the medical image reading professional candidate to participate in reading sets of medical images of anatomical regions in which the medical image reading professional candidate has qualified to participate.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF DRAWINGS

Figure 1:
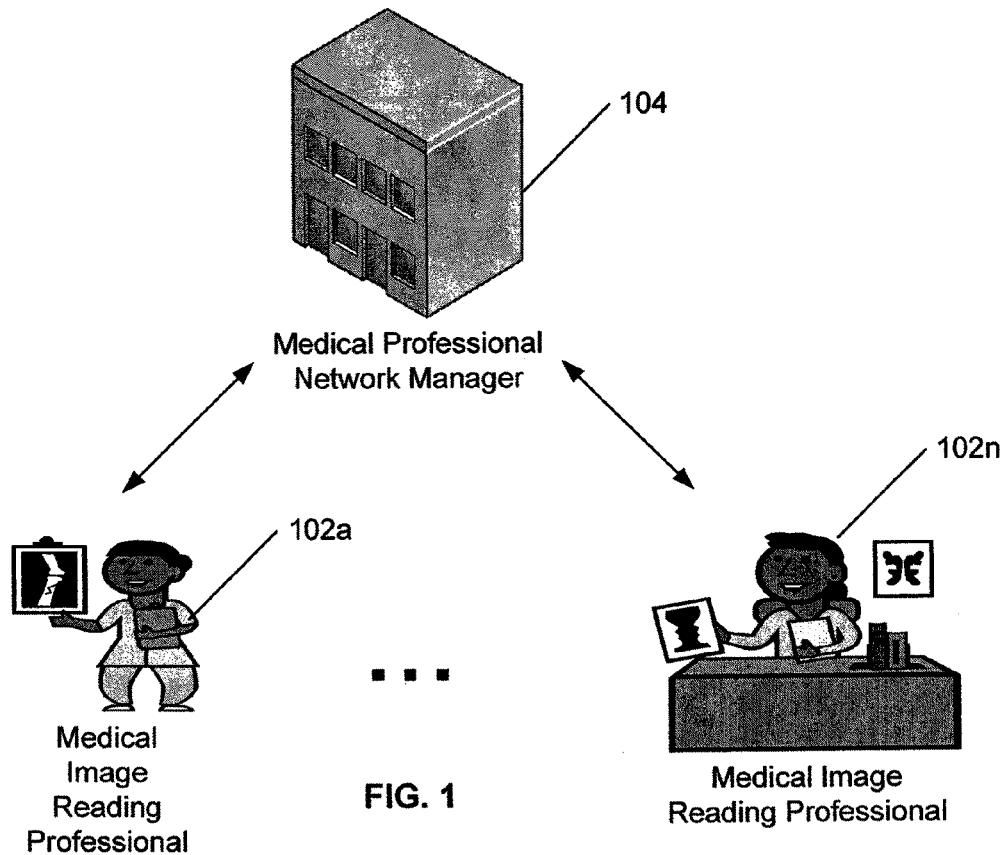
FIG. 1 is an illustration of a manager of a network of medical image reading professionals.

FIG. 1 is an illustration of a network 100 of medical image reading professionals 102a-102n (collectively 102). The medical image reading professionals 102 may be radiologists, medical doctors, or any other medical professional who reads and diagnoses medical conditions, such as diseases, of patients by reading medical images. A medical professional network manager 104 may create the medical image reading professional network 100 using a variety of techniques. In one embodiment, the medical professional network manager 104 establishes predetermined acceptance criteria for the medical professionals 102 who apply to participate in the medical image reading professional network 100. The predetermined acceptance criteria may be a minimum number of medical images of a specific modality for a defined anatomical region and/or clinical need read by a medical image reading professional on an annual or other time duration basis, a certain number of years of work experience, or other predetermined acceptance criteria that the medical professional network manager 104 may consider relevant as to predicting a proficiency skill level for a medical image reading professional. Alternative or combinations of predetermined criteria may be utilized in creating the medical image reading professional network, but by using predetermined acceptance criteria, the medical image reading professional network may be established with medical image reading professionals meeting at least one criterion for having a certain level of competence for accurately diagnosing medical conditions of patients.

As understood in the art, there are many different types of medical images. It should also be understood that the most proficient medical image reading professionals tend to be experts in reading the different types of medical images. It should further be understood that it takes a different amount of time to read and create a diagnosis from various different types of medical images, and that different levels of expertise and experience are needed to obtain competence in reading the various types of medical images. However, proficiency of medical image reading professionals can be determined, where proficiency is the ability for a medical image reading professional to accurately interpret information related to medical images in order to diagnose a medical condition. Further, characteristics of proficient reading professionals can be used to construct predictive models for identifying other proficient reading professionals.

Figure 2:
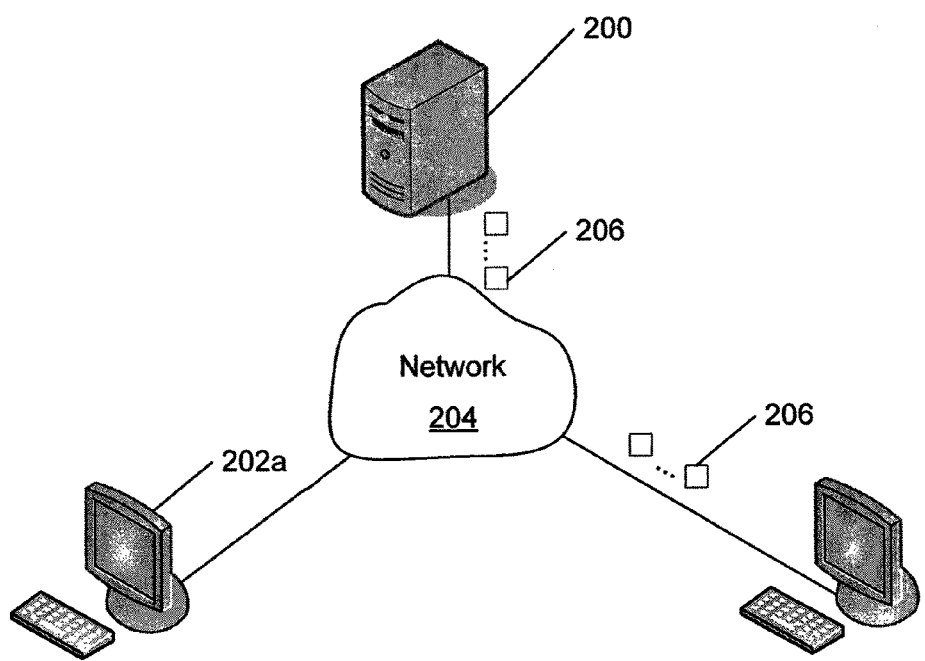
FIG. 2 is a block diagram of a server that enables medical image reading professionals to be tested to participate in a medical image reading professionals network via computers on a communications network.

FIG. 2 is a block diagram of an exemplary server 200 that enables medical image reading professionals to be tested to participate in a medical image reading professionals network via computers 202a-202n (collectively 202) on a communications network 204. The server 200 may be operated by a medical professional network manager, such as medical professional network manager 104 of FIG. 1. The server 200 may be a web server configured to operate a website on the network 204. In one embodiment, the network 204 is the Internet or other network that enables wireline and wireless communications. The server 200 may communicate data over the network 204 using data packets 206, as understood in the art. Alternative communications protocols may be utilized. The medical image reading professionals may use the computers 202 to interact with the server 200 to apply for and/or be tested to participate in the medical image reading professionals network.

Figures 3, 4:
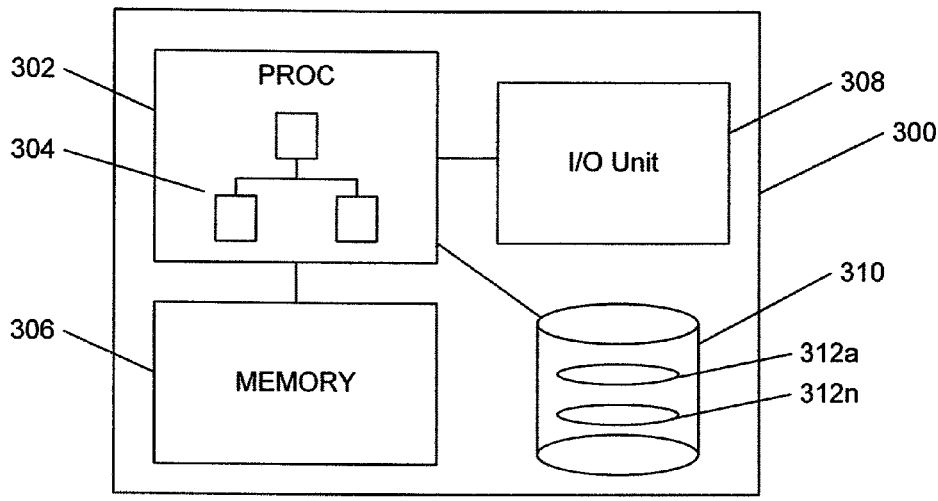
FIG. 3 is a block diagram of an exemplary server configured to gather information from and test medical image reading professional candidates who apply to participate in a medical image reading professionals network.
FIG. 4 is a screen shot of an exemplary graphical user interface that enables a medical image reading professional candidate to apply to participate in the medical image reading professionals network.

FIG. 3 is a block diagram of an exemplary server 300 configured to test medical image reading professional candidates who apply to participate in a medical image reading professional network. The server 300 may include a processing unit 302, which may include one or more computer processors. The processing unit 302 may execute software 304 that is configured to operate a website on the Internet or other network. The processing unit may be in communication with memory 306, input/output (I/O) unit 308, and storage unit 310. The memory 306 may be utilized to store data during operation of the software 304. The I/O unit 308 may be configured to communicate using one or more communications protocols over a network with computers or communication devices, such as handheld communications devices, operated by medical image reading professionals.

The storage unit 310 may store one or more data repositories 312a-312n (collectively 312). The data repositories 312 may include a database or other type of data repository configured to store information associated with medical image reading professionals, sets of medical images, characteristics or tendencies of medical image reading professionals that have predictive value relative to proficiency, and test questions and answers. The sets of medical images may include one or more medical images of an anatomical region of a patient that show a medical condition or show a normal condition. Each set of medical images may be any type of medical images for which the medical professional network manager desires to test proficiency of medical image reading professionals. Each set of medical images may be of the same or different anatomical region of the same or different patient. The test questions and answers may include questions associated with content contained in sets of medical images and answers may provide the correct answers that the server 300 uses to evaluate or grade the answers by the medical image reading professionals who apply to participate in the medical image reading professionals network.

In operation, when a potential medical image reading professional candidate wants to apply for the medical image reading professionals network, the software 304 being executed by the processing unit 302 may provide a webpage (see FIG. 4) for the medical image reading professional candidate to request information, such as contact information, medical training information, work experience information, expertise selection information, and any other information desired by the medical professional network manager. Because it is understood that medical image reading professionals have limited ability to be proficient at being an expert for more than a defined number of disease states, anatomical regions, imaging modality combinations area of expertise, the medical image reading professional candidates are asked to select area of expertise in which he or she wants to focus. In one embodiment, the software 304 may initially determine from the information submitted by the medical image reading professional candidate whether he or she meets predetermined acceptance criteria to be admitted into the medical image reading professionals network. For example, more than 5,000 medical image readings of one specific area of expertise per year may qualify a medical image reading professional candidate to be in the medical image reading professionals network, while 10,000 medical image readings may qualify a medical image reading professional for a different area of expertise. The number of medical image readings per year may vary depending on the particular area of expertise that the medical image reading professional candidate selected. Alternatively, the information submitted by the medical image reading professional may be collected by the software 304 and stored in the data repositories 312 for the medical professional network manager to evaluate. If the medical professional network manager determines that the medical image reading professional candidate is qualified to apply to participate for the medical image reading professionals network, then the software 304 may be configured to communicate by posting a message, emailing, or otherwise, with the medical image reading professional candidate to notify him or her that he or she may take a qualifying examination.

In providing for the medical image reading professional candidate to take the qualifying examination, the software 304 may access the sets of medical images and test questions stored in the data repositories 312. The software 304 may further access the sets of medical images associated with the areas of expertise selected by the medical image reading professional candidate. In the event that the medical image reading professional candidate selected multiple areas of expertise, then the software 304 may test the medical image reading professional candidate for each area of expertise individually or mix the different expertise areas during the examination. In one embodiment, the software 304 may display the sets of medical images and associated test questions on a webpage (see FIG. 5) or otherwise communicate the sets of medical images and associated questions to the medical image reading professional candidate (e.g., via email) from the server 300 via the I/O unit 308 over a communications network to a computer operated by the medical image reading professional. The sets of medical images may be communicated one at a time or all together.

The test questions associated with the sets of medical images may be multiple choice questions, as understood in the art, and may enable the medical image reading professional candidate to read the associated set of medical images and provide answers to the test questions. In addition, the test questions may be relevant to predicting or assessing proficiency not directly related to a medical image. One or more correct answers may be associated with each of the multiple choice questions. In another embodiment, the questions may be essay questions that allow for the medical image reading professional to provide freeform answers in diagnosing medical condition(s) provided in the sets of medical images and other relevant matters. The answers, whether multiple choice, freeform, or otherwise, may be collected by the software 304 and stored in the data repositories 312 in association with the information of the medical image reading professional for the software 304 and/or medical professional network manager to grade. It should be understood that any type of test questions may be utilized to test the skill and knowledge of medical image reading professional candidates or to evaluate the absence, presence or degree to which the candidate possesses characteristics or tendencies with predictive value relative to proficiency. It should further be understood that the examination may be time limited. For example, if 100 sets of medical images are used for the test, then the medical image reading professional candidate may be limited to 10 hours to answer the questions associated with the sets of medical images. It should further be understood that grading of the exam may be weighted the same or differently for different questions. The software 304 may be configured to manage the testing and grading of the medical image reading professional candidates.

Although the test for medical image reading professional candidates has been described above as being communications network based, it should be understood that the principles of the present invention also provide for non-communications network based testing to occur. In other words, a testing or examination may be performed using paper or other medium having copies of sets of medical images with the associated questions printed or displayed thereon. If the examination is given on a paper medium, communication of the sets of medical images may be performed by distributing the sets of medical images on paper or other media, such as film. While testing using paper in a controlled testing environment may limit the ability for any type of unauthorized assistance that may occur, for efficiency and cost purposes, network delivered testing may be utilized and provided in either controlled (e.g., in a testing center) or uncontrolled (e.g., at home) environments.

FIG. 4 is a screen shot of an exemplary graphical user interface (GUI) 400 that enables a medical image reading professional candidate to apply to participate in the medical image reading professionals network. The GUI 400 may be a webpage on a website that enables a medical image reading professional to apply to participate in the medical image reading professionals network. The GUI 400 may include a variety of requesting information, including: (i) personal information 402, (ii) education information and credentials 404, and (iii) professional experience information 406. Additional information may be collected as well.

The personal information 402 may include name, address, telephone number, email address, and other contact information. Depending on the amount of scrutiny that the medical professional network manager desires, social security number and other information that may be used to perform a background check, such as credentials, malpractice history, criminal or financial background check, may be requested.

The education information 404 may include undergraduate, graduate, medical school information, or any other type of schooling (e.g., expertise fellowship). The schooling information may be used to determine the quality of education that the medical image reading professional received. In addition, the certification number and other identification information may be requested to enable the medical professional network manager to perform background checks to verify credentials, malpractice history, governmental or other payor status, or other complaint has been filed against the medical image reading professional in the past or is currently ongoing.

The professional experience information 406 may include number of years experience, number of medical imaging reads performed on an annual or other time duration (e.g., weekly or monthly) basis, and expertise area(s) that the medical imaging professional candidate focuses or considers him or herself an expert. Other professional experience information may be collected, including types of medical images typically read, types of medical imaging equipment typically utilized, and other professional experience information.

The GUI 400 may further provide for the medical image reading professional candidate to select one or more expertise area(s), shown in exemplary list 408, in which he or she considers himself or herself qualified to function in the medical image reading professionals network. The medical image reading professional candidate may click on a selectable GUI element 410, such as a check-box, radio button, drop-down menu, or any other selectable GUI element as understood in the art. The anatomical region expertise areas provided may include any anatomical region in which medical image reading professionals perform image readings and diagnoses. Once the medical image reading professional candidate has completed filling in the information and selecting one or more expertise areas, the medical image reading professional may click on a "submit" soft-button 412 to submit the information.

The list 408 may have alternative and more detailed embodiments. Because the human body is so complex and because there are so many subtleties that a medical image reading professional needs to identify to make correct diagnoses for each anatomical region, the principles of the present invention provide for a list that may be organized generally by anatomical (body) region, where expertise may exist on the part of the reader, whether that expertise is in the reading or interpretation of MRI, CT or another imaging modality. An alternative list, as shown in TABLE I may include sub-sections that denote categories of disease process that are common in these anatomical regions, which may benefit from expertise to diagnose or characterize the findings seen on medical images presented to the medical image reading professional. For example, some neuro-radiologists may have expertise in reading MRI of the brain, and some subset of these radiologists may have very significant experience in reading MRI of the brain to discern the presence of multiple sclerosis, or MRI changes that might suggest progression of existing multiple sclerosis.

By providing a more extended list with sub-sections for various anatomical regions, candidate medical image reading professionals who are registering to join the medical image professionals network may be more selective in defining their medical image reading expertise. Moreover, the medical image reading professionals network manager may be provided with the ability to provide medical images during testing that are more specific and difficult to scrutinize the medical image reading professional candidates.

TABLE I

| Medical Imager Expertise Areas: | Sub-Sections: |
| --- | --- |
| Head | Head: |
| Neck | Trauma |
| Shoulder | Tumors |
| Chest | White Matter (Multiple sclerosis) |
| Heart | Vacular conditions (AVM, |
| Foot | Aneurysm) |
| Knee | Heart: |
| Hip | Coronary artery disease |
| Hand | Cardiac valvular disease |
| Vascular | Cardiac Dysmorphology |
| Abdomen | Chest: |
| Pelvis | Pulmonary |
| Spine | Nodule/Mass |
|  | Interstitial lung disease |
|  | Pulmonary infectious processes |

As described with regard to FIG. 3, the information may be stored in a data repository and software and/or medical professional network manager may review the submitted information to determine whether the medical image reading professional candidate is qualified to participate in the medical image reading professionals network.

Figure 5:
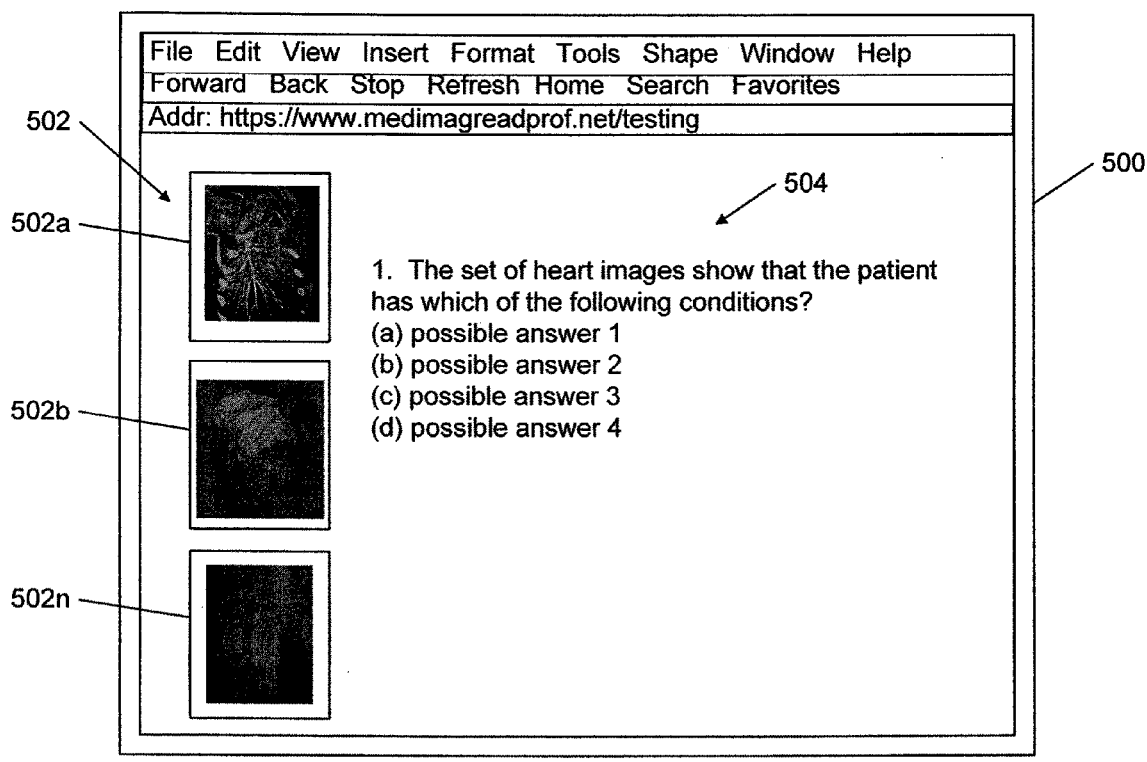
FIG. 5 is a screen shot of an exemplary graphical user interface that may be used to test proficiency of medical image reading professional candidates in diagnosing medical conditions contained in medical images of patients.

FIG. 5 is a screen shot of an exemplary GUI 500 that may be used to test proficiency of medical image reading professionals in diagnosing medical conditions contained in sets of medical images of patients. The GUI 500 shows a set of medical images 502 including images 502a-502n including different views of a heart for a multiple choice question 504. There may be one or more questions for each set of medical images and each set of medical images may include one or more images from which a medical image reading professional candidate is to answer one or more questions. Each of the possible answers may be selectable via entering a letter or number, for example, in a text entry field, selecting the answer itself (e.g., using a computer mouse or touch screen to touch on the words an answer), or otherwise as understood in the art. Each of the medical images may be selectively magnified, rotated, color adjusted, or otherwise altered in the same or different window to enable a medical image reading professional candidate to be able to read the sets of medical images and answer the associated question(s). The GUI 500 may present the medical images and questions in any format, as understood in the art.

Figure 6:
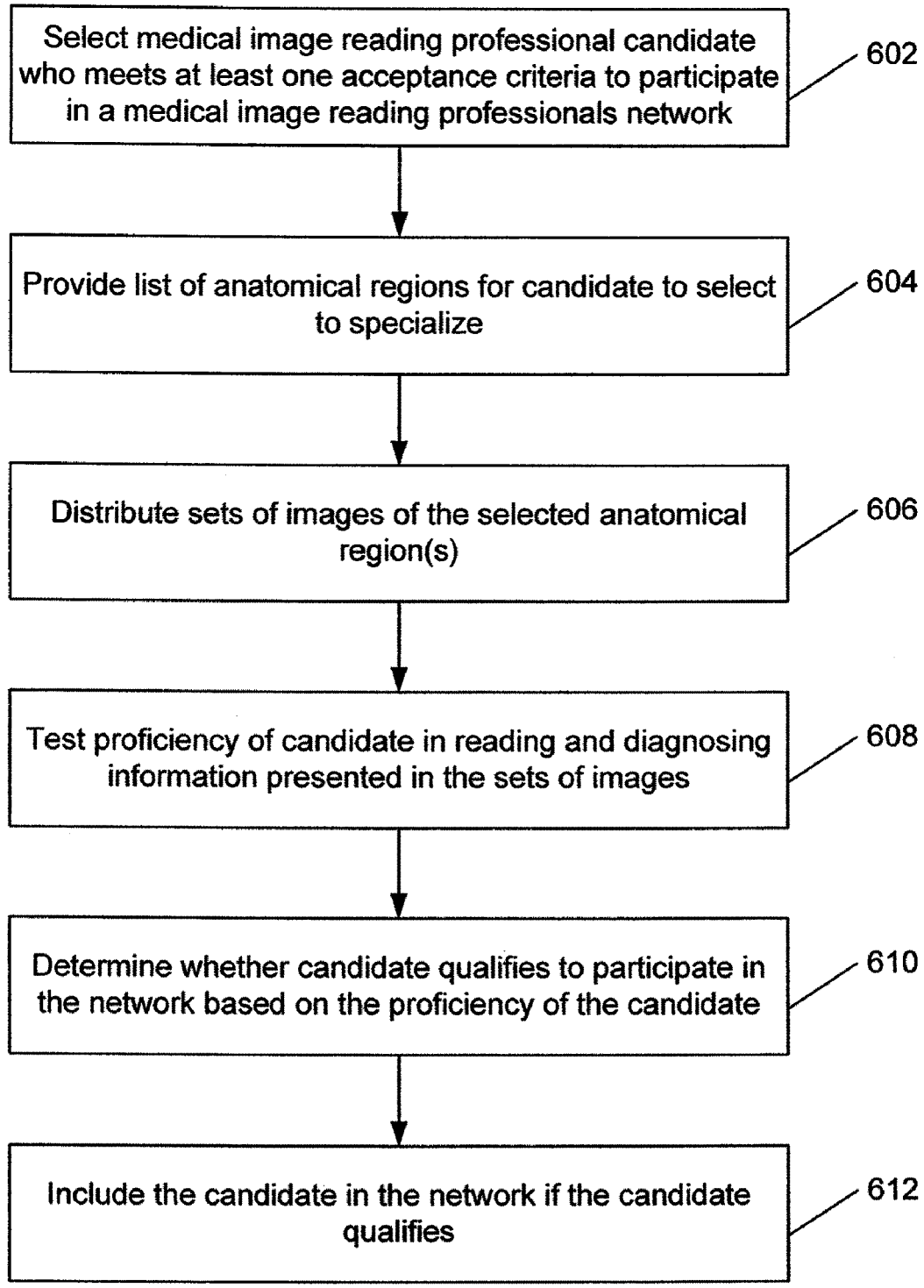
FIG. 6 is a flow diagram of an exemplary process for creating a medical image reading professionals network.

FIG. 6 is a flow diagram of an exemplary process 600 for creating a medical image reading professionals network. The process 600 may start at step 602, where a medical image reading professional candidate who meets at least one acceptance criteria may be selected. In selecting the medical image reading professional candidate, a software program or individual may review information submitted by a medical image reading professional. The acceptance criteria may include number of years of reading medical images, predetermined number of medical images read per year or other time duration, caliber of school, or any other acceptance criteria. The acceptance criteria may vary for different medical image reading expertise areas (e.g., 20,000 per year for knees and 5,000 per year for brains). At step 604, a list of areas of expertise for the selected medical image reading professional candidate may be provided for the medical image reading professional candidate to select at least one areas of expertise to focus in participating in a network of medical image reading professionals. The list may be provided on a webpage, on paper, via a telephone, or any other form of communication.

Sets of medical images of the selected area(s) of expertise may be distributed to the medical image reading professional candidate at step 606. The sets of medical images distributed may be associated with one or more area of expertise selected by the medical image reading professional candidate. If the medical image reading professional candidate is being tested via a network, then the sets of medical images may be distributed via the network by displaying or posting on a website, emailing, or other method of communicating the images to the medical image reading professional candidate. In one embodiment, the sets of medical images may be available for the medical image reading professional candidate to access for a limited duration of time. In other words, the medical image reading professional candidate may be limited to 10 hours of access once he or she begins testing, thereby giving a time limit for taking an examination.

At step 608, proficiency of the medical image reading professional candidate in reading and diagnosing information presented in the distributed sets of medical images may be tested. In one embodiment, the medical image reading professional candidate may be tested with a time limit to read and diagnose patients from the sets of medical images distributed to the medical image reading professional candidate. At step 610, it may be determined whether the medical image reading professional candidate qualifies to participate in the network of medical image reading professionals for the selected at least one area of expertise based on the proficiency of the medical image reading professional candidate in reading and diagnosing information presented in the distributed sets of medical images. In qualifying, a grade of the examination taken by the medical image reading professional candidate may be determined, where a passing grade (e.g., at least 80% correct) qualifies the medical image reading professional to participate in the medical image reading professionals network and a non-passing grade does not qualify the medical image reading professional to participate in the medical image reading professionals network.

At step 612, if the medical image reading professional candidate qualifies to participate in the network of medical image reading professionals, the medical image reading professional candidate may be included or admitted in the network of medical image reading professionals to enable the medical image reading professional candidate to participate in reading medical images in the area of expertise in which the medical image reading professional candidate has qualified to participate. In including the medical image reading professional candidate into the network of medical image reading professionals, a user profile may be created for the medical image reading professional candidate that includes information to enable the medical image reading professional candidate to access medical images and performing reading and diagnoses of patients. The user profile may include an identifier associated with the medical image reading professional candidate, password, or any other information that may allow the medical professional network manager to verify that the medical image reading professional is to have access to medical images of patients.

Although the detailed description and drawings are directed to creating a network of medical image reading professionals, the principles of the present invention should not be limited to creating a network of medical image reading professionals. Rather, the principles of the present invention may be utilized to create a network of medical professionals who perform tasks that are capable of being tested to determine proficiency of the medical professionals to create a network of highly skilled medical professionals. The network of medical professionals may be used in processing medical information, such as blood samples, to diagnose patients.

The previous detailed description of a small number of embodiments for implementing the invention is not intended to be limiting in scope. One of skill in this art will immediately envisage the methods and variations used to implement this invention in other areas than those described in detail. The following claims set forth a number of the embodiments of the invention disclosed with greater particularity.

What is claimed is:

1. A method for creating a network of medical image reading professionals, said method comprising;
   providing a list of expertise areas for a medical image reading professional candidate to select, via a computing device, at least one expertise area to focus in participating in a network of medical image reading professionals;
   selecting the candidate by selecting a medical image reading professional candidate who meets at least one criteria prior to the medical image reading professional being allowed to select from the list, the at least one criteria including performing at least a predetermined number of medical image readings per year;
   distributing, via an electronic medium, sets of medical images of the selected at least one expertise area to the medical image reading professional candidate;
   testing, on the computing device, proficiency of the medical image reading professional candidate in reading and diagnosing information presented in the distributed sets of medical images;
   determining whether the medical image reading professional candidate qualifies to participate in the network of medical image reading professionals for the selected at least one expertise area based on the proficiency of the medical image reading professional candidate in reading and diagnosing information presented in the distributed sets of medical images; and
   if the medical image reading professional candidate qualifies to participate in the network of medical image reading professionals, including the medical image reading professional candidate in the network of medical image reading professionals to enable the medical image reading professional candidate to participate in reading medical images of the at least one expertise area in which the medical image reading professional candidate has qualified to participate;
   otherwise, not including the medical image reading professional candidate in the network of medical image reading professionals.

2. The method according to claim 1, wherein selecting a medical image reading professional candidate who performs at least a predetermined number of medical image readings per year includes selecting a medical image reading professional candidate who performs at least 5,000 medical image readings per year.

3. The method according to claim 1, wherein providing a list of areas of expertise includes providing a list on a graphical user interface having at least one area of expertise being selectable.

4. The method according to claim 1, wherein distributing the sets of medical images includes posting the sets of medical images on a website available for the medical image reading professional candidate to access for a limited duration of time.

5. The method according to claim 1, wherein testing proficiency of the medical image reading professional candidate includes:
   providing selectable multiple choice answers from which the medical image reading professional candidate selects to diagnose medical conditions of patients from whom the distributed sets of medical images were taken; and
   receiving selection submissions from the medical image reading professional candidate of diagnoses of the medical conditions of the patients.

6. The method according to claim 1, wherein determining whether the medical image reading professional candidate qualifies to participate in the network includes:
   grading the selection submissions from the medical image reading professional candidate; and
   determining whether the grade of the medical image reading professional candidate is at or above a threshold grade.

7. The method according to claim 1, further comprising establishing a user profile for the medical image reading professional candidate if he or she qualifies to participate in the network, at least a portion of the user profile enabling the medical image reading professional candidate to access images of areas of expertise of patients for which the medical image reading professional candidate has selected and is qualified.

8. The method according to claim 1, wherein distributing the sets of medical images includes distributing radiological images.

9. The method according to claim 1, wherein providing the list includes providing a list that includes sub-sections of anatomical regions organized by categories of disease process or condition common in each respective sub-section of anatomical region.

10. A system for creating a network of medical image reading professionals, said system comprising:
    a storage unit including a data repository, the data repository storing sets of medical images of at least one area of expertise, each of the sets of medical images being taken from patients having known medical conditions;

an input/output (I/O) unit configured to provide communications over a communications network;

a processing unit in communication with said storage unit and I/O unit, and configured to communicate with the data repository to access the stored images, said processing unit further configured to:

operate a network site on which a medical image reading professional candidate applies to participate in a network of medical image reading professionals;

provide access to the medical image reading professional candidate who meets at least one criteria, the at least one criteria includes performing at least a predetermined number of medical image readings per year;

in response to the medical image reading professional candidate applying to participate in the medical image reading professionals network via the communications network, communicate via communications network a list of areas of expertise for the medical image reading professional candidate to select at least one area of expertise to focus in participating in the medical image reading professionals network;

communicate sets of medical images of the selected at least one area of expertise to the medical image reading professional candidate;

test proficiency of the medical image reading professional candidate in diagnosing information presented in the distributed sets of medical images;

determine whether the medical image reading professional candidate qualifies to participate in the medical image reading professionals network for the selected at least one area of expertise based on the proficiency of the medical image reading professional candidate in diagnosing information presented in the distributed sets of medical images; and if the medical image reading professional candidate qualifies to participate in the medical image reading professionals network, include the medical image reading professional candidate in the medical image reading professionals network to enable the medical image reading professional candidate to participate in reading medical images of anatomical regions in which the medical image reading professional candidate has qualified to participate;

otherwise, not include the medical image reading professional candidate in the network of medical image reading professionals.

11. The system according to claim 10, wherein the predetermined number of medical image readings per year is 5,000.

12. The system according to claim 10, wherein said processing unit, in testing proficiency of the medical image reading professional candidate, is configured to:

provide selectable multiple choice answers from which the medical image reading professional candidate selects to diagnose medical conditions of patients from whom the distributed sets of medical images were taken; and receive selection submissions from the medical image reading professional candidate of diagnoses of the medical conditions of the patients.

13. The system according to claim 10, wherein said processing unit is configured to receive the selection submissions for a limited duration of time.

14. The system according to claim 10, wherein said processing unit, in determining whether the medical image reading professional candidate qualifies to participate in the medical image reading professionals network, is configured to:

grade the selection submissions from the medical image reading professional candidate; and determine whether the grade of the medical image reading professional candidate is at or above a threshold grade.

15. The system according to claim 10, wherein said processing unit, in including the medical image reading professional candidate in the medical image reading professionals network, is configured to establish a user profile for the medical image reading professional candidate, at least a portion of the user profile enabling the medical image reading professional candidate to access images of area of expertise of patients for which the medical image reading professional candidate has selected and is qualified.

16. The system according to claim 10, wherein the sets of medical images are radiological images.

17. The system according to claim 10, wherein the list includes sub-sections of anatomical regions organized by categories of disease process or condition common in each respective anatomical region.

* * * * *